United States Patent
Niiyama et al.

[11] Patent Number: 5,993,740
[45] Date of Patent: *Nov. 30, 1999

[54] IMMUNOASSAY METHOD AND ANALYZER USING MAGNETIC PARTICLES

[75] Inventors: Yasushi Niiyama, Mito; Hiroyasu Uchida; Ryuji Tao, both of Hitachinaka, all of Japan

[73] Assignee: Hitachi, Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/896,156

[22] Filed: Jul. 17, 1997

Related U.S. Application Data

[63] Continuation of application No. 08/376,012, Jan. 20, 1995, abandoned.

[51] Int. Cl.[6] .................................................. G01N 33/553
[52] U.S. Cl. .......................... 422/52; 209/215; 209/217; 210/222; 210/695; 422/101; 435/7.92; 435/287.2; 435/288.7; 436/526; 436/538; 436/824
[58] Field of Search ..................................... 436/526, 538, 436/172, 801, 805, 806, 807, 823, 824; 435/7.1, 7.92, 173.1, 174, 287.2, 288.7, 961, 962, 968; 422/52, 101; 209/215, 217; 210/695, 222

[56] References Cited

U.S. PATENT DOCUMENTS

| | | |
|---|---|---|
| 5,053,344 | 10/1991 | Zborowski et al. . |
| 5,068,088 | 11/1991 | Hall et al. . |
| 5,240,863 | 8/1993 | Shibue et al. . |
| 5,466,416 | 11/1995 | Ghaed et al. . |
| 5,536,475 | 7/1996 | Moubayed et al. . |
| 5,541,072 | 7/1996 | Wang et al. . |
| 5,705,402 | 1/1998 | Leland et al. . |

FOREIGN PATENT DOCUMENTS

93/01308  1/1993  WIPO .

*Primary Examiner*—Jan Ludlow
*Attorney, Agent, or Firm*—Frohwitter

[57] ABSTRACT

Magnetic particles are used as the solid phase to carry out immunoassay. In a reaction vessel, the magnetic particles are mixed with a sample containing TSH as an analyte and a labeled antibody. A chemiluminescent label material is bound onto the magnetic particles with an immunoreaction. A fluid including the above mixture is introduced to a chamber inside a flow through cell, the chamber being sized to have a width greater than a depth. The magnetic particles in the fluid are trapped by a magnet so as to be spread in the planar form over a predetermined area within the chamber, while useless materials are discharged outwardly of the chamber. The chamber is then filled with a buffer solution containing an attractant. By applying a voltage to electrodes disposed in the chamber, the label material on the magnetic particles is excited to emit an electro-chemiluminescence. The luminescence is detected by a photomultiplier.

6 Claims, 12 Drawing Sheets

$$\left( \alpha = 45°, \frac{W_2}{W_1} = 10, v = 60 \text{mm/s}, t = 1.0 \text{mm} \right)$$

IMMUNOASSAY METHOD AND ANALYZER USING MAGNETIC PARTICLES

This application is a continuation under 37 CFR §1.60 of prior application Ser. No. 08/376,012, filed Jan. 20, 1995, now abandoned.

BACKGROUND OF THE INVENTION

The present invention relates to a method and an apparatus for immunoassay utilizing the reaction between an antigen and an antibody, and more particularly to an analyzing method and an analyzer in which magnetic particles are used as the solid phase for an immunoreaction.

The immunoreaction forming an immunocomplex is employed to determine antigens and antibodies in biological samples such as serum and urine. When reacting the solid phase and the liquid phase, it is customary to employ a labeled antibody as a reagent and to measure the liquid phase after the reaction by using a detector. Known examples of the label are a radioisotope, an enzyme, a colored particle, a fluorescent material, a luminescent material, etc.

Japanese patent laid-open Hei-3-46565 teaches enzyme immunoassay which is performed by using magnetic particles coated with a polymer having a reactive radical. The absorbance or the fluorescent intensity of the liquid phase is measured in this prior art.

WO 87/06706 teaches, as label agents, many examples of materials emitting a chemiluminescence and materials emitting an electro-chemiluminescence. It is suggested that, of those materials, an organic compound of ruthenium or osmium is preferable as a label for the electro-chemiluminescence. This prior art also teaches that, after an immunoreaction is progressed using magnetic particles as the solid phase, the solid phase is magnetically separated from the liquid phase and an electro-chemiluminescence is measured for the liquid phase. Such a process of separating the bound component and the free component is called B/F separation.

While the above two prior arts measure the liquid phase, U.S. Pat. No. 4,141,687 teaches it to measure a label on the solid phase. More specifically, in U.S. Pat. No. 4,141,687, magnetically attractable particles are used as the solid phase, a radioactive atom is used as the label, and an immunoreaction is progressed in a flow path. After the immunoreaction, a reaction mixture is introduced to flow through a magnetic trap. At this time, the liquid phase passes through the magnetic trap, but the solid phase is held in the trap. After washing, the solid phase is released from the magnetic trap and then introduced along a conduit to pass through a downstream coil, followed by measurement of its radioactivity by a scintillation counter.

SUMMARY OF THE INVENTION

An object of the present invention is to provide an immunoassay method and analyzer by which, when magnetic particles are used as the solid phase, a luminescence from the solid phase can be measured with high sensitivity.

Another object of the present invention is to provide an immunoassay method and analyzer in which the number of times of transferring the solid phase is small and the operation of treating the solid phase is simple.

Still another object of the present invention is to provide an immunoassay method and analyzer by which the solid phase can be kept at rest in a place where an electro-chemiluminescence is emitted from the solid phase.

The immunoassay method according to the present invention comprises the steps of labeling a chemiluminescent label material on magnetic particles through an immunoreaction, flowing a fluid containing the magnetic particles through a chamber sized to have a width larger than a depth under a condition where a magnetic field is applied to the chamber, holding the magnetic particles introduced with a flow of the fluid in the planar spread form by magnetic force within the chamber, and receiving a luminescence emitted from the label material on the magnetic particles in a direction parallel to the chamber depth.

In a preferred embodiment, in the step of holding the magnetic particles, the magnetic particles are distributed over a working electrode disposed in the chamber. After releasing the magnetic field applied to the chamber, a voltage is applied between the working electrode and a counter electrode while the magnetic particles remain held on the working electrode,, causing the label material to emit an electro-chemiluminescence.

DESCRIPTION OF THE PREFERRED EMBODIMENT

Figure 1:
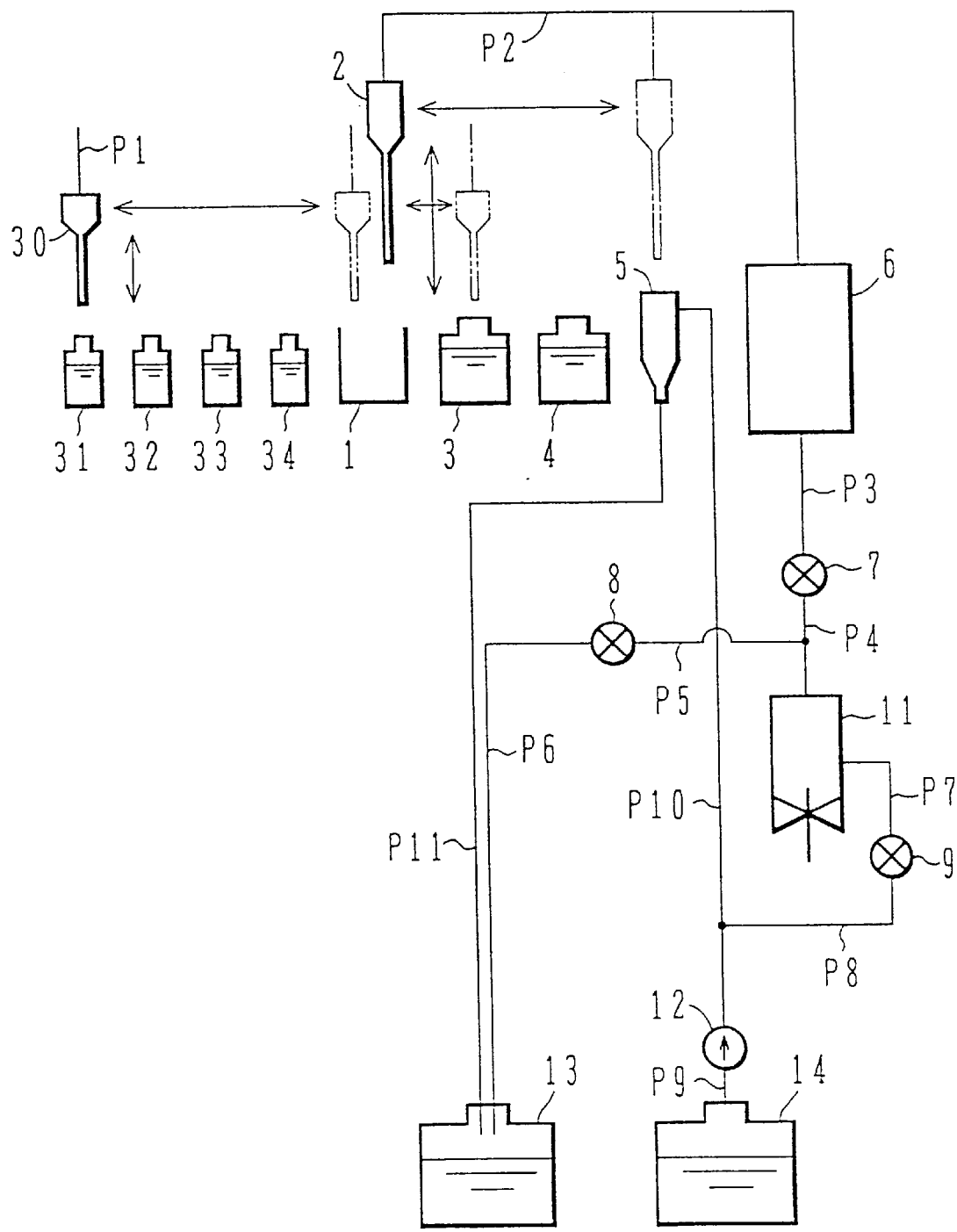
FIG. 1 is a diagram schematically showing the entire arrangement of an immunoassay method according to one embodiment of the present invention.

When a sample is serum, an analyte, i.e., an object to be analyzed, is an antigen, peptide hormone, steroid hormone, a medical reagent, a virus antibody, various tumor markers, an antibody, an antibody complex, protein, etc.

Magnetic particles as the solid phase has a particle size of 1 to 10 $\mu$m and specific weight of 1.3 to 1.5. The magnetic particles are hard to precipitate in a fluid and are apt to be suspended in the fluid. An antibody is fixed to the particle surface. The magnetic particles are formed by embedding powder of magnetically attracting materials, e.g., iron, iron oxide, nickel, cobalt and chromium oxide, in a matrix. The matrix itself can be selected from among a wide range of materials including many synthetic and natural polymeric materials (e.g., cellulose and polyester).

With the progress of an immunoreaction, an immunocomplex containing an analyte and a luminescent label is bound onto the magnetic particles. The immunocomplex is introduced to a flow chamber of a flow through cell together with other coexisting materials in a reaction mixture (i.e., a suspension).

The magnetic particles are trapped in a predetermined place by magnetic force in the planar spread form within the chamber, but the magnetic force is released at the time of measuring a luminescence. Since the flow of the fluid in the chamber is stopped at this time, the magnetic particles remain in the same form as trapped by the magnetic force within the chamber.

The flow chamber is formed such that its width is two to twenty times as large as its depth (thickness). With this configuration of the chamber, the magnetic particles introduced with the flow of the fluid are facilitated to spread horizontally. It is ideal that the magnetic particles are spread in the form of a single layer, but the particles are practically overlapped with each other to some extent. In this specification, the term "planar spread form" also includes such a case of the particles being overlapped with each other. The spreading of the particles into the planar form within the chamber depends on not only the intensity of the magnetic force, but also the flow velocity of the reaction mixture when it is introduced to the chamber. If the force induced by the flow velocity exceeds the magnetic force for holding the particles, the particles would be dislodged from the magnetically immobilized positions. It is therefore required to select the appropriate flow velocity.

The magnetic particles once held in the chamber are washed by a buffer solution. The flow velocity of the buffer solution during the washing is set to be equal to or less than the flow velocity of the reaction mixture when introduced.

The magnetic flux density of a magnet for applying a magnetic field to the chamber is preferably in the range of 0.5 to 3 T. The measuring cell, i.e., the flow through cell, has a light permeable window between the chamber and a photodetector. The window is made of any one selected from among glass, quartz and plastics, such as acrylate and polycarbonate, having light permeability not less than 90%. The photodetector is one selected from among a photomultiplier, an avalanche photodiode, a photodiode and a streak tube. The window may be in the form of a convex lens.

In the measuring cell, separating reaction products from the liquid phase in the suspension is performed by using magnetic trap means in the flow chamber inside the measuring cell placed at a predetermined position in the conduit. The suspension is introduced to the flow chamber inside the measuring cell along the conduit by feed means for sucking or delivering the suspension. When the suspension reaches the region of a local magnetic field produced by a magnet disposed below or above the working electrode, the reaction products in the suspension are trapped by the magnetic force on the working electrode.

The conditions to be satisfied in the step of introducing the suspension to the flow chamber inside the measuring cell and trapping the reaction products on the working electrode are as follows. To increase the luminescent efficiency of a label material, the largest possible part of the reaction products in the suspension introduced through the conduit should be trapped on the working electrode with good reproducibility, and the trapped reaction products should be ideally dispersed in a single layer uniformly over a wide area.

The flow chamber is structured such that it has a spindle-like shape as viewed from above, a width of the spindle-like shape at its maximum width portion is within seven times an inlet diameter (minimum width portion) of the chamber, an opening angle of the chamber as viewed from its inlet toward the maximum width portion is not greater than 20°, and a thickness of the chamber is in the range of 0.3 to 0.7 mm. If the flow chamber has an improper shape, the flow would be apt to peel off and air bubbles would be apt to reside near lateral surfaces of the flow chamber, thereby disturbing the reaction products in the suspension in its trapping onto the working electrode, and a washing fluid would not reach the lateral surfaces of the flow chamber when the reaction products once trapped are washed out, making it difficult to wash out the reaction products after the luminescent reaction.

In consideration of rendering contaminants, such as protein, in the sample to be less deposited on chamber walls and preventing deterioration of the chamber walls caused by the washing fluid, etc. to the extent possible, a material of members forming the flow chamber is selected from electrically non-conductive materials such as ethylene tetrafluoride, butyl rubber, silicone rubber, glass and acrylic resin.

For the magnetic particles having a particle size of 2 to 3 $\mu$m, when the suspension containing the reaction products is introduced to the flow chamber, a flow condition is optimized by setting the linear velocity of the suspension to be in the range of 10 to 100 mm/s, and a larger amount of the reaction products can be trapped on the working electrode in the uniformly dispersed form. If the linear velocity is lower than 10 mm/s, the reaction products in the suspension would be concentrated to one point on the working electrode when trapped, making it difficult to ensure the high luminescent efficiency in the step where the reaction products emit an electro-chemiluminescence. If the linear velocity is higher than 100 mm/s, it would be so hard to trap the reaction products on the working electrode that most of the reaction products would pass through the chamber, resulting in lack of the luminescence intensity.

The solid phase, which contains the reaction products trapped on the working electrode when the suspension passes through the flow chamber inside the measuring cell, can be washed by flowing a washing fluid into the flow chamber through the conduit. The solid phase remains trapped on the working electrode, while the reaction products are exposed to the washing fluid flowing through the chamber for washing thereof.

Taking into account a luminescent reaction in the next step, the washing fluid is preferably a buffer solution containing an attractant which serves to excite the label material. The purposes of using the buffer solution are to remove the residue of the liquid phase in the suspension from the trapped solid phase, and to supply the attractant for attracting excitation of the label material around the reaction products with good reproducibility.

The magnetic particles are trapped by a local magnetic trap which is produced by a magnet placed above the working electrode when the working electrode is disposed along an upper surface of the flow chamber, or below the working electrode when it is conversely disposed along a lower surface of the flow chamber. The working electrode may be disposed along any of the upper and lower surfaces of the flow chamber, but it is desirable from the viewpoint of trapping efficiency and easiness of installation that the working electrode be disposed along the lower surface of the flow chamber and in the maximum width portion of its spindle-like shape. Also, the surface area of the working electrode is preferably within three times, more preferably one to two times, as large as the area necessary for the reaction products bound to the magnetic particles when they are arranged adjacent each other to lie in a single layer as dense as possible.

The shape of the working electrode is selected from among a circle, a square and an ellipse with the major axis extending in a direction of the flow passage depending on the magnet shape. By selecting one of the above shapes, the reaction products can be trapped on the smaller electrode area with higher efficiency. Taking into account the shape of a photoelectric surface of the photodetector (which is circular for the head-on type detector), any of the above shapes is also suitable for enabling the photodetector to detect a luminescence emitted by an electro-chemical reaction on the working electrode with high efficiency.

A material of the working electrode and a counter electrode is any one selected from among gold, platinum, palladium, tungsten, iridium, nickel and alloys of thereof. The reason of using such a material is to prevent wear and corrosion of the electrode surface caused respectively by the electrode reaction and reagents flowing over the electrode to the extent possible.

The working electrode and the counter electrode are disposed on the same plane with a distance not greater than 3 mm therebetween and, where applicable, the counter electrode is disposed in pair on both sides of the working electrode in symmetrical relation. With this arrangement, the working electrode and the counter electrode can be easily installed in the measuring cell and, when a voltage is applied between the working electrode and the counter electrodes, the voltage can be efficiently and stably applied to opposite end faces of the working electrode. Therefore, the attractant for attracting excitation of the label material can be always surely formed with good reproducibility.

The local magnetic trap for distributing the magnetic particles analogously to the shape of the electrode surface is produced by at least one magnet installed on the side of the flow chamber inside the measuring cell opposite to the working electrode. It is desirable that the magnet can be approached to 0.5 to 3 mm from the surface of the working electrode and also can change the trapping magnetic field from a minimum value to a maximum value as needed. This is practiced by moving the magnet away from the working electrode such that the working electrode surface is subject to no magnetic field or close to the working electrode conversely when the magnet is a permanent magnet, and by de-energizing or energizing the magnet when it is an electromagnet. By so switching the magnet field, the reaction products which are bound to the magnetic particles trapped on the working electrode and still remain on the working electrode can be washed out with high efficiency after the electro-chemical luminescent reaction. Further, by setting the magnetic flux density of the magnet to be in the range of 0.5 to 3 T, the area of the magnet surface (on the side facing the working electrode) to be 0.5 to 3 times the surface area of the working electrode, and the shortest distance between the magnet and the working electrode surface to be in the range of 0.5 to 3 mm, an optimum magnetic field can be locally applied to the reaction products in the suspension flowing through the conduit and the flow chamber. As a result, a larger amount of the reaction products in the reaction suspension can be trapped in more uniform distribution over a wider area with good reproducibility.

After the reaction products have been trapped onto the working electrode surface, the non-reacted reagent can be quickly washed out with high efficiency by flowing a buffer solution through the flow chamber under such a trapped condition. Therefore, the B/F separation can be simply achieved with the minimum carryover. To this end, the magnet is preferably disposed right below or above the working electrode, respectively, when the working electrode is placed along the lower or upper surface of the flow chamber.

After being washed by the buffer solution and separated from the non-reacted liquid phase, the reaction products trapped on the working electrode are subject to voltages applied between the working electrode and the counter electrode in accordance with a certain sequence so that the attractant contained in the buffer solution and attracting excitation of the label material are reduced. The label material is excited by the reduced attractant and then transited into the ground state, whereupon it emits a luminescence of predetermined wavelength. The emitted luminescence enters a light permeable window provided on the side of the flow chamber inside the measuring cell opposite to the working electrode, and is then introduced to a detecting portion of the photodetector disposed in contact with the window (or with a certain distance therebetween in some cases) for measuring the luminescence intensity. The window is preferably sized to have an area at least four times the surface area of the working electrode. By constructing the measuring cell based on the above-described conditions, when the luminescence intensity is measured by the photodetector, the weak light emitted on the working electrode can be introduced to the photodetector with high efficiency, enabling the measurement of a luminescence to be achieved with high accuracy and good reproducibility.

By using the measuring cell constructed as described above, specific components in living body samples, such as serum and urine, can be analyzed in a quick and simple manner with high sensitivity and good reproducibility.

Hereinafter, an immunoassay method and analyzer according to one embodiment of the present invention will be described with reference to FIGS. 1 to 12.

A description will be first made of the system configuration of the analyzer of this embodiment with reference to FIG. 1.

In FIG. 1, the analyzer of this embodiment comprises a sample bottle 31 containing a sample, a beads bottle 32 containing a beads solution which includes magnetic particles, a first reagent bottle 33 containing a first reagent for binding the magnetic particles to a specific component in the sample, a second reagent bottle 34 containing a second reagent for labeling a label material which emits a luminescence due to an electro-chemical reaction, and being bound to the specific component in the sample, a buffer solution bottle 3 containing a buffer solution which includes an attractant for attracting an electro-chemiluminescence from the label material, a washing fluid bottle 4 containing a washing fluid, a reaction vessel 1 for producing a suspension which contains reaction products, a sampling probe 30 for pipetting the sample, the beads, the first reagent, the second reagent and the buffer solution into the vessel 1, a sipper probe 2 for feeding the suspension in the vessel 1, a washing tank 5 for washing a tip end of the sipper probe 2, a measuring cell 6 to which the suspension fed from the sipper probe 2, a syringe 11 for sucking and delivering the suspension, the washing fluid and the buffer solution, a waste fluid bottle 13 containing a waste fluid, a distilled water bottle 14 containing a distilled water, and a pump 12 for feeding the distilled water in the distilled water bottle 14 to the washing tank 5.

The sampling probe 30 has a known pipetting mechanism and is connected to a syringe (not shown) through a conduit P1. The sipper probe 2 is connected to the measuring cell 6 through a conduit P2. The measuring cell 6 is connected to the syringe 11 through a conduit P3, a first pinch valve 7 and a conduit P4. Further, the conduit P4 is connected to the waste fluid bottle 13 through a conduit P5, a second pinch valve 8 and a conduit P6.

On the other hand, the distilled water bottle 14 is connected to the washing tank 5 through a conduit P9, a pump 12 and a conduit P10, while the washing tank 5 is connected to the waste fluid bottle 13 through a conduit P11. Also, a conduit P8 is branched from midway the conduit P10 and is connected to the syringe 11 through a third pinch valve 9 and a conduit P7.

The sample in the sample bottle 31 is, e.g., serum or urine that is obtained from the living body and contains TSH (Thyroid Stimulating Hormone) as a specific component.

The beads solution in the beads bottle 32 is prepared by embedding a particulate magnetic material in a matrix made of polystyrene or the like to obtain each of beads, i.e., magnetic particles (specific weight 1.4, mean particle size 2.8 $\mu$m), and then dispersing the magnetic particles in a buffer solution. Fixed to the matrix surface is streptoavidin which is capable of binding to biotin. The magnetic particles may each contain a plurality of particulate magnetic materials in the matrix.

The first reagent in the first reagent bottle 33 contains a TSH antibody whose end is biotinized.

The second reagent in the second reagent bottle 34 contains a TSH antibody whose end is biotinized and to which a label material emitting a chemiluminescence upon excitation is fixed. In this embodiment, Ru(bpy)$_3$, i.e., ruthenium (II) tris(bipyridil), is used, by way of example, as the label material. Ru(bpy)$_3$ is present in the form of Ru(bpy)$_3^{2+}$ in the buffer solution.

The buffer solution in the buffer solution bottle 3 contains an attractant which is reduced upon application of a voltage so as to excite the label material, and has a pH value of about 7.4. In this embodiment, tripropylamine (TPA) is used as the attractant.

The structure of the measuring cell will be described below with reference to FIGS. 2 to 4.

The measuring cell 6 comprises a cell base plate 18, a PMT case 21 housing a photomultiplier (PMT) 19 therein, and a light receiving window 22 positioned between the cell base plate 18 and the PMT case 21. The cell base plate 18 and the light receiving window 22 are held together with a spacer 18A interposed therebetween, so that a flow chamber 17 through which the suspension containing the reaction products flows after being introduced to the measuring cell 6 is defined between the plate 18 and the window 22. The flow chamber 17 has, as shown in FIG. 4, a spindle-like shape as viewed from above. A flow passage inlet 35 is positioned at one end of the spindle-like shape, and a flow passage outlet 36 is positioned at the other end thereof. The flow passage inlet 35 and outlet 36 are connected respectively to the conduits P2, P3 through nipples 50, 51 attached to the cell base plate 18. A working electrode 15 is disposed along a lower surface of the flow chamber 17 in its central maximum width portion of the spindle-like shape, and a pair of counter electrodes 16a, 16b are disposed in symmetrical relation on both sides of and in the same plane as the working electrode 15. The working electrode 15 and the counter electrodes 16a, 16b are attached to a sheet member 18B disposed on the cell base plate 18, and are extended at their one ends outwardly of the cell base plate 18 for connection to a power supply and a controller (both not shown). A magnet 24 is positioned below the working electrode 15 and is disposed in a recess 18C formed in the cell base plate 18 so that it may come close to the working electrode 15. The magnet 24 is attached to a magnet holder 25 which is in turn attached to one end of a lever 25A. The other end of the lever 25A is attached to a stepping motor 26 so as to be turnable about a support point 28. By energizing the stepping motor 26, the magnet 24 can selectively take an operative position, indicated by solid lines, within the recess 18C and a retracted position, indicated by two-dot-chain lines, outside the recess 18C.

The photomultiplier 19 measures a luminescence generated in the flow chamber 17 and passing through the light receiving window 22, and this embodiment employs R1104 manufactured by Hamamatsu Photonics Co., Ltd. To prevent a reduction in the multiplying efficiency due to magnetism, the photomultiplier 19 is housed in the PMT case 21 in such a condition that it is covered by a shield tube 20. Attached to an upper end of the photomultiplier 19 is a socket 27 through which a detection signal of the photomultiplier 19 is sent to the controller (not shown) for measuring the luminescent intensity.

The sheet member 18B defining the lower surface of the flow chamber 17 is formed of an ethylene tetrafluoride polymer. The flow chamber 17 is formed such that a minimum width $W_1$ at opposite ends of the spindle-like shape is 1 mm, a maximum width $W_2$ at the center is 5 mm, a length L of the chamber is 33 mm, an opening angle $\alpha$ is 16.2°, and a thickness t is 0.5 mm. The flow passage inlet 35 and outlet 36 of the flow chamber 17 each have a diameter of 1 mm that is equal to the minimum width $W_1$.

Figure 3:
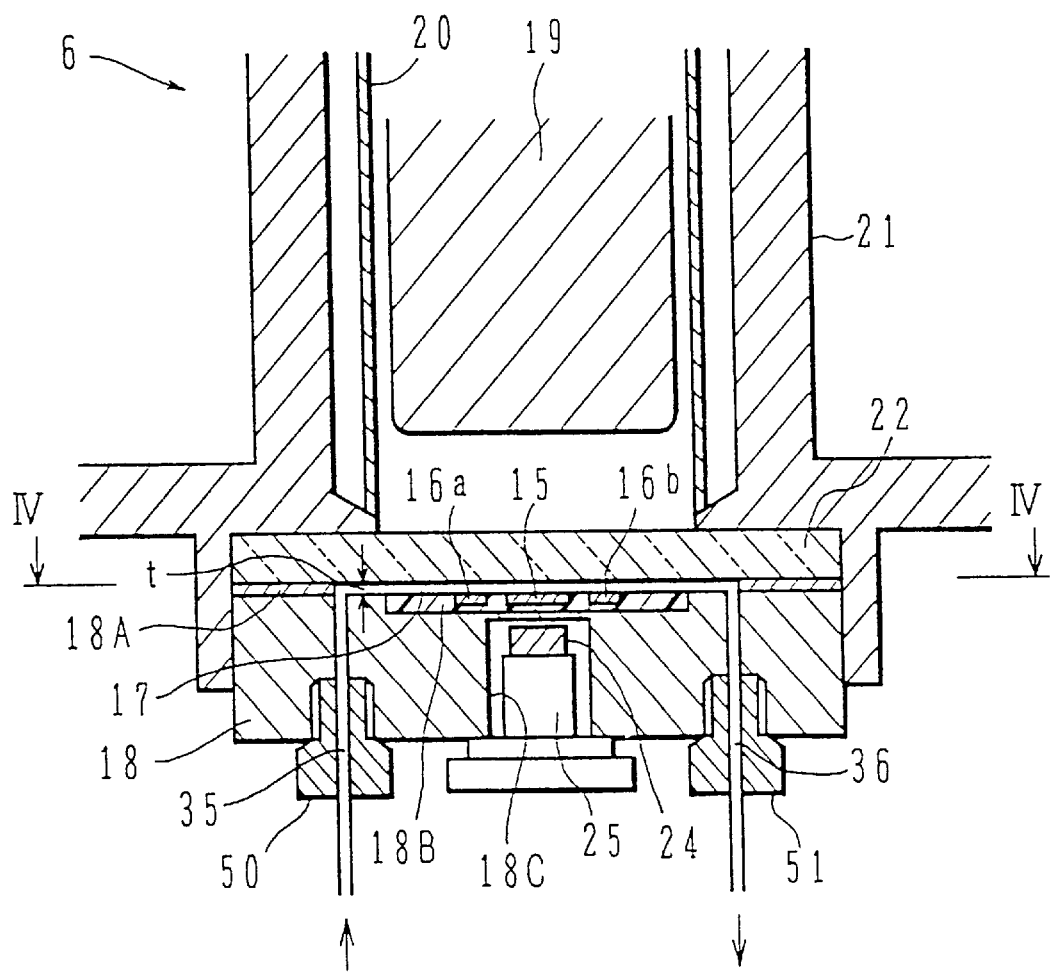
FIG. 3 is a partial enlarged view of the measuring cell of FIG. 2.
Figure 4:
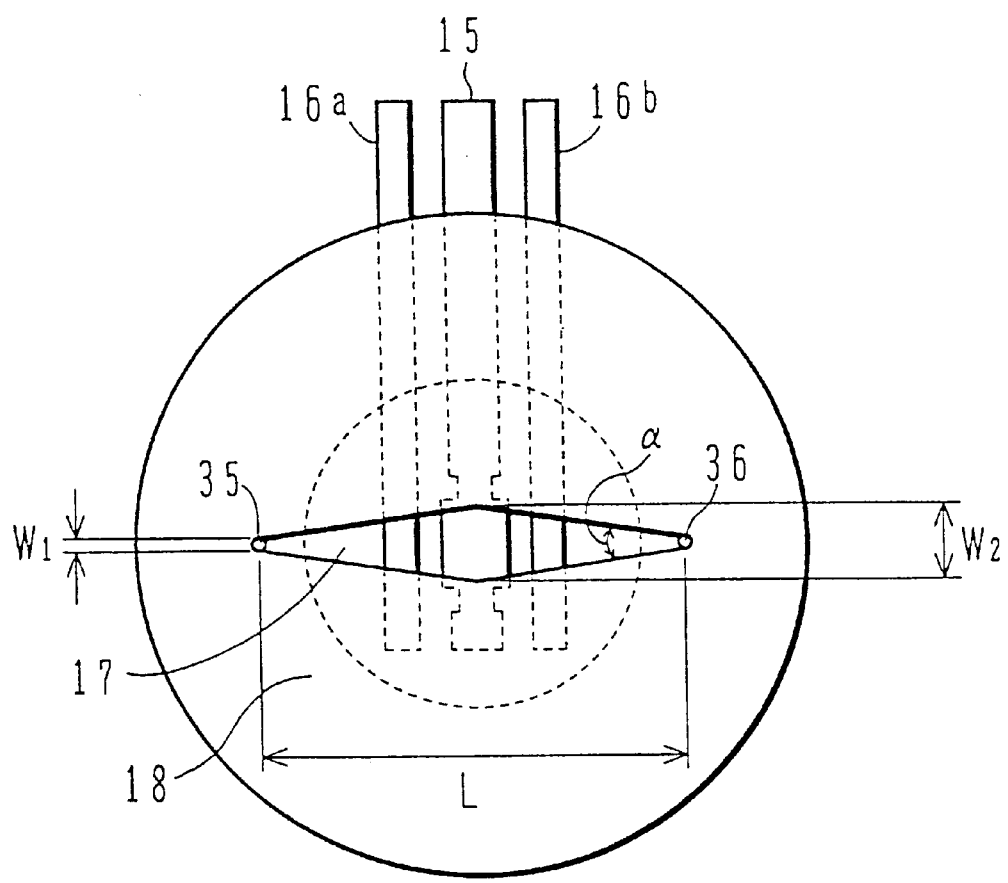
FIG. 4 is a sectional view taken along line IV—IV in FIG. 3.
Figure 5A:
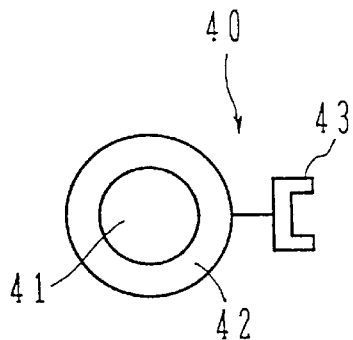
FIGS. 5A–5F are views showing, in the form of models, a magnetic particle, a first reagent, an analyte in a sample, a second reagent, a reaction product, and an attractant.
Figure 5B:
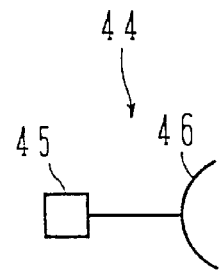
Figure 5C:
Figure 5D:
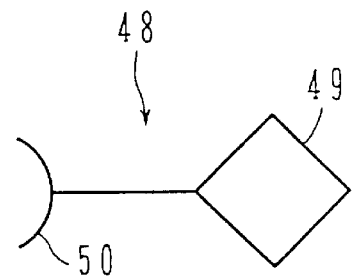
Figure 5E:
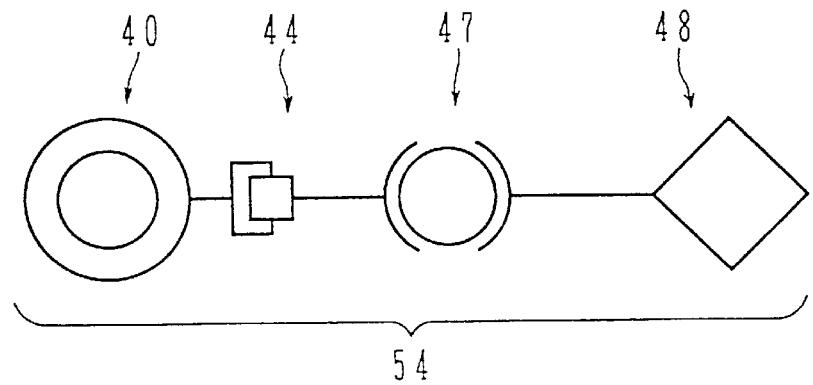
Figure 5F:
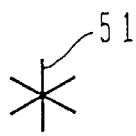

The working electrode 15 is made of platinum and, as shown in FIGS. 3 and 4, its portion exposed to the flow chamber is square in a plan view such that a width is 5 mm and an area is 25 mm$^2$. If the aforesaid magnetic particles having the mean particle size of 2.8 $\mu$m are arranged on the working electrode 15 to lie adjacent each other in a single layer as dense as possible, about 3.7×10$^6$ particles can be accommodated. Assuming that the magnetic particles dispersed in the buffer solution contained in the beads bottle 32 is used in amount of 30 $\mu$g for each cycle, this amount corresponds to the magnetic particles of about 2×10$^6$. Thus, the surface area of the working electrode 15 is about 1.85 times the area necessary for the magnetic particles used in each cycle to spread into the planar form.

Each of the counter electrodes 16a, 16b is also made of platinum as with the working electrode 15 and is disposed with a spacing of 1 mm from the working electrode 15.

The magnet 24 is a square permanent magnet having each side of 5 mm and is magnetized to have an N pole facing the working electrode 15 with a magnetic flux density of 0.85 T. In the operative position within the recess 18C, the magnet 24 is located with a distance of 1 mm from the surface of the working electrode 15.

The light receiving window 22 is formed of acrylate which is a non-conductive plastic material having light permeability not less than 90%, and has a disk-like shape with a thickness of 4 mm and an effective diameter of 25 mm.

The operation of the immunoassay analyzer constructed as above will be described below.

50 μl of the living body sample, such as serum or urine, which is put in the sample bottle 31 and contains TSH (Thyroid Stimulating Hormon) as the specific component, 50 μl of the beads solution which is put in the beads bottle 32 and contains the magnetic particles (30 μg) dispersed in the buffer solution, 50 μl of the first reagent which is put in the first reagent bottle 33 and contains the TSH antibody whose end is biotinized, 50 μl of the second reagent which is put in the second reagent bottle 34 and contains the TSH antibody whose end is biotinized and to which the label material emitting a chemiluminescence upon excitation is fixed, and 50 μl of the buffer solution which is put in the buffer solution bottle 3, contains the attractant, and has a pH value of about 7.4, are pipetted by the sampling probe 30 into the vessel 1 in accordance with a predetermined sequence.

Here, an example of analyzing the sample by the sandwich method will be explained. In this case, the beads solution, the first reagent, the sample and the second reagent are pipetted in this order. In the case using the competitive method, the beads solution, the sample, the second reagent and the first reagent are pipetted in this order.

During the pipetting operation, the mixture is agitated by a vibrating device (not shown) to progress the reaction while the vessel 1 is kept at a predetermined temperature (37° C. in this embodiment). Even after the pipetting operation, the mixture is continuously kept at the predetermined temperature and agitated for a predetermined period of time (15 minutes in this embodiment). As a result, a suspension is produced which contains the magnetic particles, the first reagent, TSH in the sample, and the reaction products to which the second reagent is bound. The tip end of the sampling probe 30 is washed after each pipetting operation in a like manner to washing of the tip end of the sipper probe 2 (described later).

After that, the suspension in the vessel 1 is introduced to the flow chamber 17 of the measuring cell 6. This operation of introducing the suspension is performed as follows.

Figure 2:
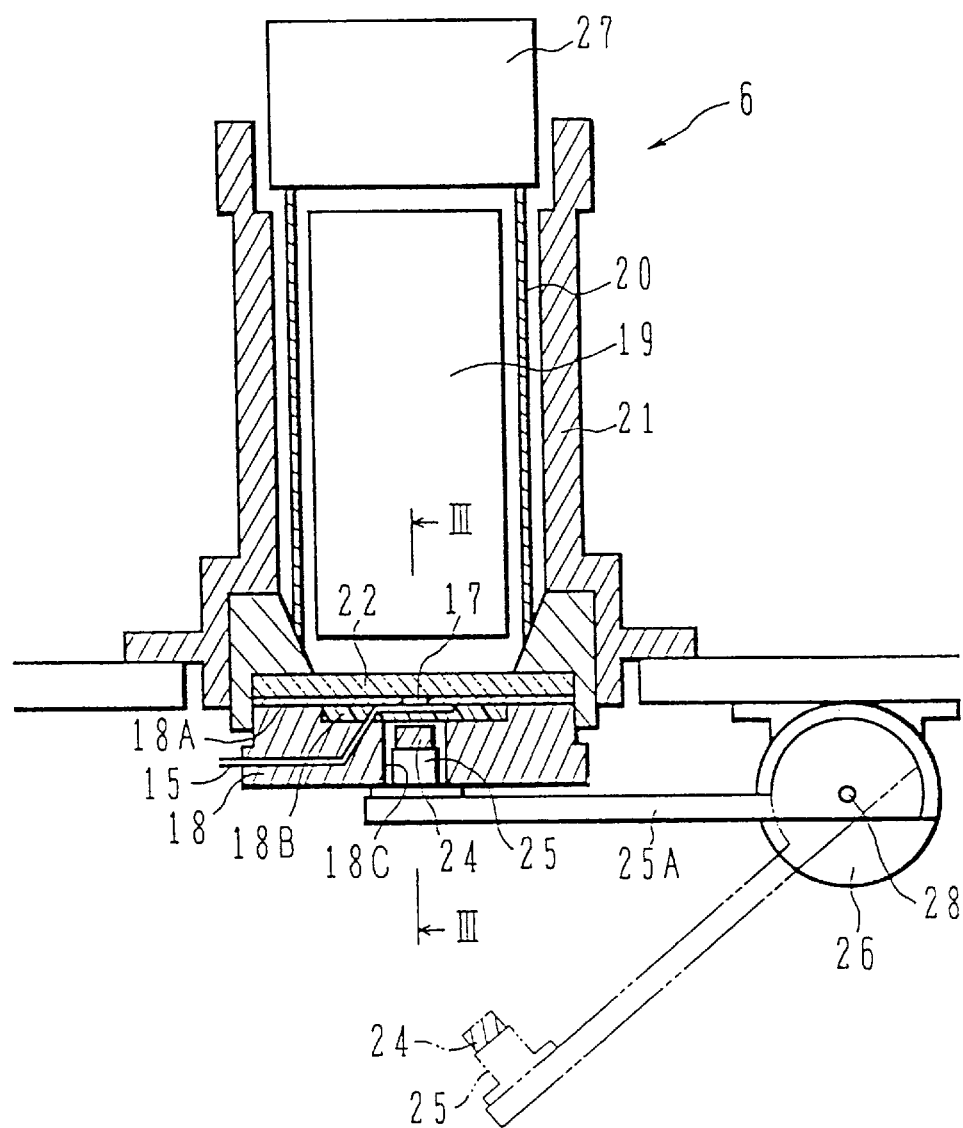
FIG. 2 is a vertical sectional view showing the construction of a measuring cell in the analyzer of FIG. 1.

First, in FIG. 2, the stepping motor 26 is driven to move the magnet 24 to the operative position indicated by solid lines in the drawing. Then, in FIG. 1, the first pinch valve 7 is opened, but the second and third pinch valves 8, 9 are closed. In this condition, the sipper probe 2 is first horizontally moved by a driving unit (not shown) to a position above the vessel 1, and is then moved downward so that its tip end is inserted to the suspension in the vessel 1.

Next, of total 250 μl of the suspension prepared in the vessel 1 and containing the reaction products, 200 μl of the suspension is sucked by the syringe 11 into the sipper probe 2. The sipper probe 2 is moved upward to such an extent that its tip end comes out of the suspension, following which the suspension in the sipper probe 2 is sucked again by the syringe 11. With this suction, 200 μl of the suspension is introduced to the measuring cell 6 through the conduit P2 and flows through the flow chamber 17. At this time, the operation of the syringe 11 is controlled so that the suspension enters the flow chamber 17 from the flow passage inlet 35 at the linear velocity of 50 mm/s. When the suspension reaches a position above the working electrode 15, only the reaction products and the non-reacted magnetic particles are trapped on the working electrode 15, whereas the non-reacted first and second reagents are sucked into the syringe 11 through the flow chamber 17. In this way, all of the reaction products contained in 200 μl of the suspension are collected to effect the B/F separation.

Subsequently, the sipper probe 2 is horizontally moved to a position above the washing tank 5, and is then moved downward so that its tip end is inserted to the washing tank 5. In this condition, the pump 12 is driven to deliver the distilled water in the distilled water bottle 14 into the washing tank 5 through the conduit P9, the pump 12 and the conduit P10, thereby washing an outer surface of the tip end of the inserted sipper probe 2. The spent distilled water delivered into the washing tank 5 is fed as a waste fluid to the waste fluid bottle 13 from the bottom of the washing tank 5 through the conduit P11.

Then, the sipper probe 2 is moved upward to such an extent that its tip end comes out of the washing tank 5, following which it is horizontally moved to a position above the buffer solution bottle 3 and is further moved downward so that its tip end is inserted to the buffer solution in the buffer solution bottle 3. Thereafter, the buffer solution in the buffer solution bottle 3 is sucked by the syringe 11 so that 100 μl of the buffer solution is introduced to the measuring cell 6. By introducing the buffer solution, the non-reacted second reagent remaining in the flow chamber 17 of the measuring cell 6 is washed out to complete the B/F separation. At this time, the buffer solution used for the washing and the non-reacted reagent are sucked into the syringe 11 from the flow chamber 17 through the conduit P3, the first pinch valve 7 and the conduit P4.

As a result of the above process, the flow chamber 17 is brought into such a condition that the reaction products and the non-reacted first reagent (magnetic particles) are trapped on the working electrode 15, and surroundings of the working electrode 15, i.e., the whole of the flow chamber 17, is filled with the buffer solution which contains TPA for attracting excitation of the label material.

On the other hand, the buffer solution and the non-reacted reagent having been sucked into the syringe 11 are discharged into the waste fluid bottle 13 with the operation of the syringe 11 by opening the second pinch valve 8 after closing the first pinch valve 7.

After the end of the above step, voltages are applied between the working electrode 15 and the counter electrodes 16a, 16b, which are disposed in the same plane as and on both sides of the former, in accordance with a predetermined sequence to thereby effect the following reactions.

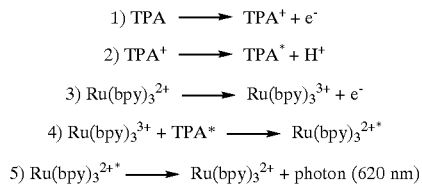

1) TPA $\longrightarrow$ TPA$^+$ + e$^-$

2) TPA$^+$ $\longrightarrow$ TPA$^*$ + H$^+$

3) Ru(bpy)$_3^{2+}$ $\longrightarrow$ Ru(bpy)$_3^{3+}$ + e$^-$

4) Ru(bpy)$_3^{3+}$ + TPA$^*$ $\longrightarrow$ Ru(bpy)$_3^{2+*}$

5) Ru(bpy)$_3^{2+*}$ $\longrightarrow$ Ru(bpy)$_3^{2+}$ + photon (620 nm)

In other words, by applying the voltages, TPA in the buffer solution is reduced and Ru(bpy)$_3^{2+}$ as the label material in the reaction products emits a luminescence. The luminescence generated from the above reactions is introduced to the photoelectric surface of the photomultiplier 19 through the light receiving window 22, which is disposed to define the upper surface of the flow chamber 17 and is light permeable, for measurement of the luminescence intensity. The measured luminescence intensity is compared with the result obtained by measuring a control material having the known TSH concentration, to calculate a TSH concentration in the sample.

During the above reaction step, to reduce an influence of the magnetic field upon the multiplying efficiency of the photomultiplier, the magnet 24 provided for the purpose of trapping the reaction products, which are bound to the magnetic particles, on the working electrode 15 is moved to the retracted position where no influence of the magnetic field acts on the surface of the working electrode 15, by driving the stepping motor 28 immediately before or, if possible, immediately after the voltages are applied to emit the luminescence based on the electro-chemical reaction.

Following the luminescent reaction, the flow chamber 17 is washed. First, the first pinch valve 7 is opened, but the second and third pinch valves 8, 9 are closed. After that, the sipper probe 2, whose tip end has been washed by the distilled water beforehand in a like manner to the above-described washing step, is horizontally moved to a position above the washing fluid bottle 4 and is then moved downward so that its tip end is inserted to the washing fluid in the washing fluid bottle 4. In this condition, the syringe 11 is withdrawn to start sucking the washing fluid in the washing fluid bottle 4. At this time, aiming to increase the washing efficiency, the sipper probe 2 is preferably moved up and down to alternately suck the washing fluid and air in a predetermined amount for each stroke while the syringe 11 is being operated to suck the washing fluid. The washing fluid thus sucked is introduced to the flow chamber 17 of the measuring cell 6 through the conduit P2 to thereby wash out the buffer solution, the reaction products and the non-reacted first reagent (magnetic particles) which still remain in the flow chamber 17 after the reaction. The waste fluid and the washing fluid both sucked into the syringe 11 are discharged into the waste fluid bottle 13 by pushing the syringe 11 with the first pinch valve 7 made closed and the second pinch valve 8 made open.

After the end of the above step, the second pinch valve 8 is closed and the first pinch valve 7 is opened again, and the syringe 11 is operated to suck 1000 μl of the buffer solution containing TPA from the buffer solution bottle 3 by using the sipper probe 2 whose tip end has been washed by the distilled water beforehand, so that the washing fluid remaining in the conduit P2 and the flow chamber 17 of the measuring cell 6 is washed out. Subsequently, the conduit P2 and the flow chamber 17 are filled with the buffer solution, thereby completing the measurement of TSH for one sample.

Furthermore, an additional washing step for maintenance of the syringe 11 may be performed as follows.

After closing the first pinch valve 7, but opening the second and third pinch valves 8, 9, the pump 12 is driven to feed the distilled water from the distilled water bottle 14 to the syringe 11 through the conduit P9, the pump 12, the conduit P10, the conduit P8, the third pinch valve 9 and the conduit P7, and further feed it from the syringe 11 to the waste fluid bottle 13 through the conduit P4, the conduit P5, the second pinch valve 8 and the conduit P6. Then, the third pinch valve 9 is closed and the syringe 11 is operated so that the distilled water remaining in the syringe 11 is fed to the waste fluid bottle 13 through the conduit P4, the conduit P5, the second pinch valve 8 and the conduit P6.

The measuring principle of the analyzing method of this embodiment, which is carried out through a series of the foregoing steps, will now be described with reference to FIGS. 5A to 7F. As mentioned before, this embodiment is based on the sandwich method.

In FIGS. 5A, 5B, 5C, 5D, 5E and 5F represent respectively, in the form of models, a magnetic particle 40, a first reagent 44, TSH 47 as the specific component (analyte) in the sample, a second reagent 48, a reaction product 54, and tripropylamine (TPA) 51 as the attractant contained in the buffer solution. The magnetic particle 40 consists of a particulate magnetic material 41, a matrix 42 containing the particulate magnetic material 41, and streptoavidin 43 fixed to the surface of the matrix 42. The first reagent 44 is formed of a TSH antibody 46 to the end of which is fixed biotin 45 so that it can be bound to the streptoavidin 43 of the magnetic particle 40. The second reagent 48 is formed of a TSH antibody 50 which is capable of binding to the TSH 47 as the analyte and to the end of which is fixed $Ru(bpy)_3$ 49 as the label material.

Figure 6A:
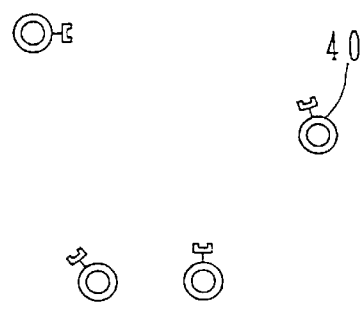
FIGS. 6A–6F are views for explaining the progress of immunoassay by the sandwich method.
Figure 6B:
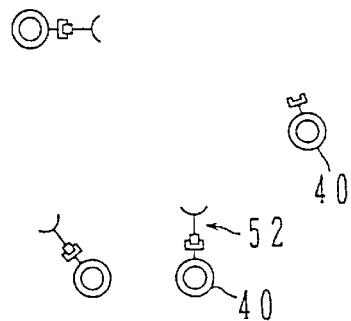
Figure 6C:
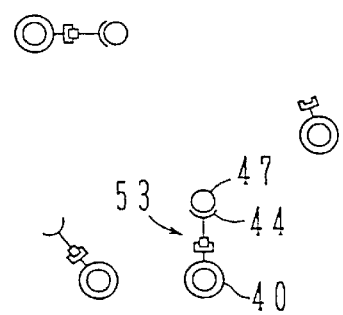
Figure 6D:
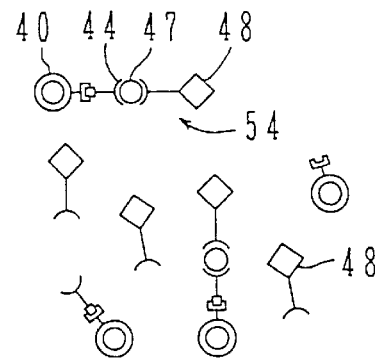

First, as shown in FIG. 6A, the beads solution in which the magnetic particles 40 are dispersed is pipetted into the reaction vessel 1. Then, when the first reagent 44 is pipetted into the vessel 1, the streptoavidin 43 on the surface of each magnetic particle 40 and the biotin 45 of the first reagent 44 are bound to each other, as shown in FIG. 6B, to produce a first complex 52 consisted of the first reagent 44 and the magnetic particle 40. At this time, the non-reacted magnetic particles 40 remain in the vessel 1. Next, when the sample containing the TSH 47 as the analyte is pipetted into the vessel 1, the TSH 47 and the TSH antibody 46 of the first complex 52 are bound to each other, as shown in FIG. 6C, to produce a second complex 53 consisted of the TSH 47 and the first complex 52. At this time, the non-reacted first complexes 52 remain in the vessel 1. After that, when the second reagent 48 is pipetted into the vessel 1, the TSH 47 of the second complex 53 and the second reagent 48 are bound to each other, as shown in FIG. 6D, to produce a reaction product 54. At this time, the non-reacted second reagent 48 remains in the vessel 1. As a result, in the vessel 1, there produces a suspension in which the reaction products 54, the non-reacted magnetic particles 40, the non-reacted first reagent 44 (first complexes 52), and the non-reacted second reagent 48 are mixed together.

Figure 6E:
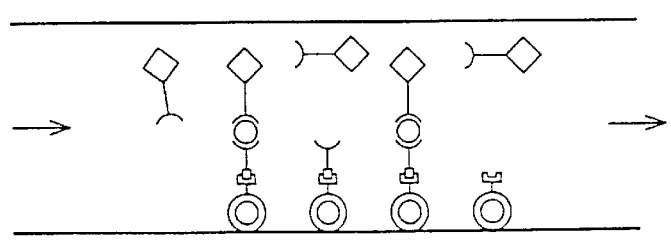
Figure 6F:
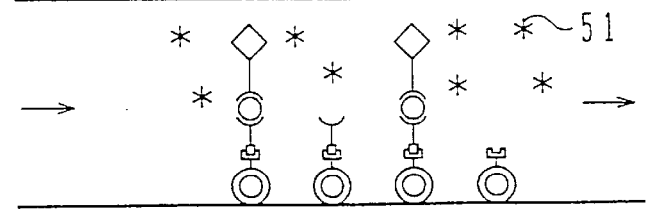

When the thus-prepared suspension containing the reaction products 54 is introduced to the flow chamber 17 of the measuring cell 6, the reaction products 54, the non-reacted first reagent 44 and the non-reacted magnetic particles 40 are magnetically trapped or seized to the lower surface of the flow chamber 17 by the magnet 24, whereas the non-reacted second reagent 48 is floated in the liquid phase filling the flow chamber 17, as shown in FIG. 6E. Subsequently, when the buffer solution is introduced to the flow chamber 17, the second reagent 48 is washed out to complete the B/F separation as shown in FIG. 6F. Simultaneously, the flow chamber 17 is filled with the TPA 51 as the attractant. After stopping the flow of the suspension, when the predetermined pulse voltages are applied between the working electrode 15 and the counter electrodes 16a, 16b, which are disposed in the same plane as and on both sides of the former, as described above, there occur the aforesaid reactions in which the TPA 51 is reduced and the label material is excited to emit the luminescence between both the electrodes. The generated luminescence passes through the light receiving window 22 disposed to define the upper surface of the flow chamber 17, and the luminescence intensity is measured by the photomultiplier 19. Prior to starting the immunoassay, the luminescence intensities of a plurality of reference materials having different TSH concentrations are measured to determine a calibration curve from the relationship between the TSH concentration and the luminescence intensity. By using the resultant calibration curve, a TSH concentration in the sample is calculated from the measured value of the luminescence intensity.

While the analyzing method of the present invention based on the sandwich method is described above, it can also be practiced by using the competitive method. The measuring principle based on the competitive method will be described below for reference.

Figure 7A:
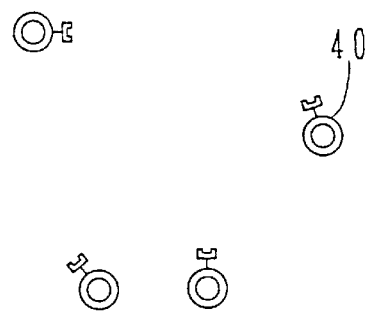
FIGS. 7A–7F are views for explaining the progress of immunoassay by the competitive method.
Figure 7B:
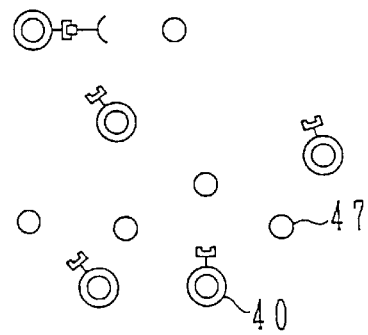
Figure 7C:
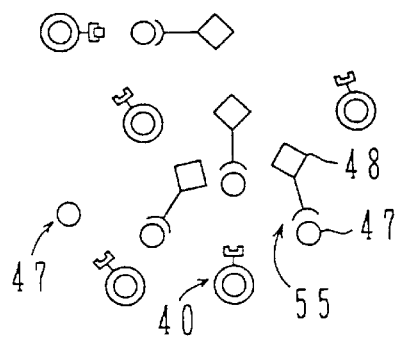
Figure 7D:
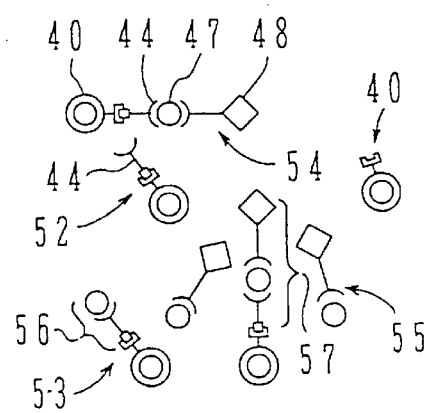

First, as shown in FIG. 7A, the beads solution in which the magnetic particles 40 are dispersed is pipetted into the reaction vessel 1. Then, the sample containing the TSH 47 is pipetted into the vessel 1 to provide a condition where the magnetic particles 40 and the TSH 47 are mixed together, as shown in FIG. 7B. Then, when a predetermined amount of the second reagent 48 is pipetted into the vessel 1 from the second reagent bottle 32, the TSH 47 and the TSH antibody 50 of the second reagent 48 are bound to each other, as shown in FIG. 7C, to produce a third complex 55 consisted of the TSH 47 and the second reagent 48. At this time, the non-reacted TSH 47 and the non-reacted magnetic particles 40 remain in the vessel 1. Next, when the first reagent 44 is pipetted into the vessel 1, the streptoavidin 43 on the surface of each magnetic particle 40 and the biotin 45 of the first reagent 44 are bound to each other, as shown in FIG. 7D, to produce the first complex 52. The sole TSH 47 and the TSH 47 of the third complex 55 are competitively bound to the TSH antibodies 46 of both the first complex 52 and the non-reacted first reagent 44 such that the first complex 52 and the sole TSH 47 are bound to produce the second complex 53, the first complex 52 and the third complex 55 are bound to produce the reaction product 54, the non-reacted first reagent 44 and the sole TSH 47 are bound to produce a fourth complex 56, and the non-reacted first reagent 44 and the third complex 55 are bound to produce a fifth complex 57. Further, the fourth complex 56 and the magnetic particle 40 are bound to produce the second complex 53, and the fifth complex 57 and the magnetic particle 40 are bound to produce the reaction product 54. As a result, in the vessel 1, there produces a suspension in which the reaction products 54, the non-reacted magnetic particles 40, the non-reacted first reagent 44 (first complexes 52), and the non-reacted second reagent 48 (third complexes 55) are mixed together.

Figure 7E:
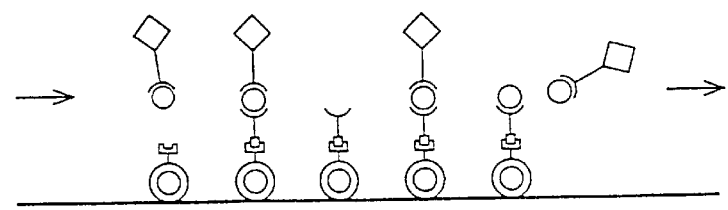
Figure 7F:
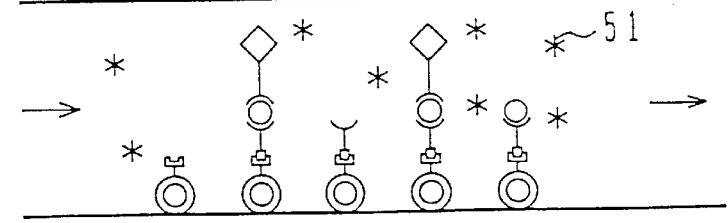

When the thus-prepared suspension containing the reaction products 54 is introduced to the flow chamber 17 of the measuring cell 6, the reaction products 54, the non-reacted first complexes 52 and the non-reacted magnetic particles 40 are magnetically trapped or seized to the lower surface of the flow chamber 17 by the magnet 24, whereas the non-reacted third complexes 55 is floated in the liquid phase filling the flow chamber 17, as shown in FIG. 7E. Subsequently, when the buffer solution is introduced to the flow chamber 17, the third complexes 55 are washed out to complete the B/F separation as shown in FIG. 7F. Simultaneously, the flow chamber 17 is filled with the TPA 51 as the attractant. After stopping the flow of the suspension, when the predetermined pulse voltages are applied between the working electrode 15 and the counter electrodes 16a, 16b, which are disposed in the same plane as and on both sides of the former, as described above, there occur the aforesaid reactions in which the TPA 51 is reduced and the label material is excited to emit the luminescence between both the electrodes. The generated luminescence passes through the light receiving window 22 disposed to define the upper surface of the flow chamber 17, and the luminescence intensity is measured by the photomultiplier 19. Prior to starting the immunoassay, the luminescence intensities of a plurality of reference materials having different TSH concentrations are measured to determine a calibration curve from the relationship between the TSH concentration and the luminescence intensity. By using the resultant calibration curve, a TSH concentration in the sample is calculated from the measured value of the luminescence intensity.

According to this embodiment, since the B/F separation and the subsequent measurement are performed in the same place, i.e., in the flow chamber 17, there is no need of transferring the reaction products after the B/F separation to the detector. Therefore, the loss incidental to transfer of the reaction products is prevented and biochemical components can be exactly and precisely analyzed with high sensitivity. Further, with no need of transferring the reaction products after the B/F separation, the operation from the B/F separation to the measurement can be simply and efficiently performed in a short period of time.

In this embodiment, the flow chamber 17 of the measuring cell 6 has a spindle-like shape as viewed from above and is designed as follows. The width $W_2$ in the central maximum width portion of the spindle-like shape is 5 mm and the diameter of the flow passage inlet of the flow chamber 17 (i.e., the width of the minimum width portion) $W_1$ is 1 mm, resulting in the ratio of $W_2/W_1=5$ (within 7 times). The opening angle α as viewed from the flow passage inlet to the maximum width portion is 16.2° (not greater than 20°) and the thickness of the flow chamber is 0.5 mm (in the range of 0.3 to 0.7 mm). With the above dimensions, a larger amount of the reaction products in the suspension introduced to the flow chamber 17 can be trapped on the working electrode with good reproducibility, and the trapped reaction products can be dispersed substantially in a single layer uniformly over a wide area on the working electrode, making it possible to increase the luminescent efficiency of the label material. In addition, the suspension introduced to the flow chamber 17 is controlled in flow rate such that its linear velocity is 50 mm/s (in the range of 10 to 100 mm/s). With this control, the flow condition can be optimized and a larger amount of the reaction products can be trapped in the more uniformly and widely spread form over the working electrode.

The working electrode 15 is positioned in the central maximum width portion of the flow chamber 17 and has a surface area about 1.85 times (within 3 times) the area required when arranging the magnetic particles introduced in each cycle so as to lie adjacent each other in a single planar layer as dense as possible. With such a structure, it is possible to trap the reaction products on the working electrode under design conditions allowing all of them to be held in the single-layer and uniform form, while minimizing the use of an expensive electrode material.

The working electrode 15 and the counter electrodes 16a, 16b are disposed on the same plane such that the counter electrodes 16a, 16b are located on both sides of the working electrode 15 in symmetrical relation with a spacing of 1 mm (not greater than 3 mm) between both the electrodes. With this arrangement, the working electrode and the counter electrodes can be easily installed in the measuring cell and, when applying a voltage between the working electrode and the counter electrodes, the voltage can be efficiently and stably applied to the opposite end faces of the working electrode. Accordingly, the material for attracting excitation of the label material, i.e., the attractant, can be always surely formed with good reproducibility.

On the other hand, the magnet 24 as magnetic trap means is a permanent magnet which is close to the working electrode 15 with a distance of 1 mm (in the range of 0.5 to 3.0 mm) in the operative position, but which can be moved away from the working electrode 15 with the aid of the lever 25A and the stepping motor 26. By so moving the magnet 24, the reaction products bound to the magnetic particles trapped on the working electrode can be efficiently washed out from there after the end of the electro-chemical luminescent reaction step. Further, the magnet 24 has a magnetic flux density of 0.85 T (in the range of 0.5 to 3 T), and also has a surface area of 5 mm×5 mm=25 mm$^2$ facing the working electrode 15, this surface area being 1 time (in the range of 0.5 to 3 times) the surface area of the working electrode 15. The distance between the magnet 24 and the working electrode surface can be as short as 1 mm. With such an arrangement, since an optimum magnetic field can be locally applied to the reaction products in the suspension flowing through the flow chamber through the conduit, a larger amount of the reaction products in the reaction suspension can be trapped in more uniform distribution over a wider area with good reproducibility.

The window 22 has an area of 490 mm$^2$ being about 20 times (at least 4 times) 25 mm$^2$, i.e., the surface area of the working electrode 15, and is made of acrylate. Through the window 22 thus formed, when measuring the luminescence intensity by the photodetector, a weak luminescence generated on the working electrode 15 can be efficiently introduced to the photodetector. As a result, the luminescence can be measured with higher accuracy and better reproducibility.

Figure 8:
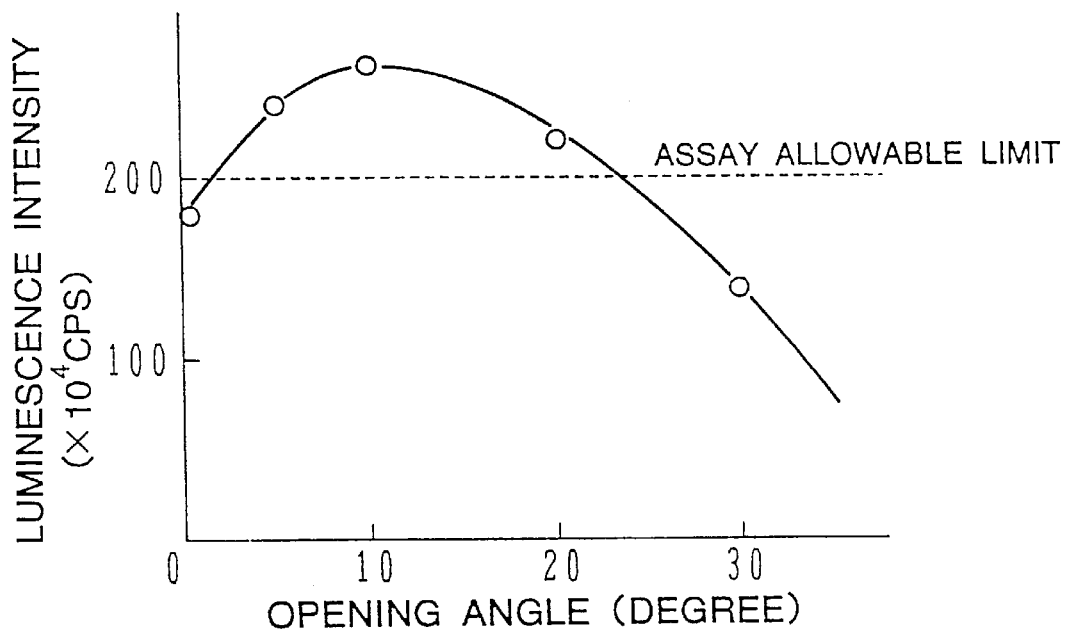
FIG. 8 is a graph of experimental results showing the relationship between the opening angle of a flow chamber and the luminescence intensity.

FIG. 8 shows results of an experiment carried out on the relationship between the opening angle α of the flow chamber 17 and the luminescence intensity. The results were obtained by measuring the luminescence intensity while changing the opening angle α on condition of the TSH concentration=1×10$^0$ μIU/ml, $W_2/W_1$=5, t=0.5 mm (basis for amendment of the units from meters to millimeters is found in the original disclosure at FIGS. 8–10), and the linear velocity v of the suspension=60 mm/s. As will be seen from FIG. 8, the luminescence intensity substantially over 200×10$^4$ cps as an assay allowable limit can be obtained at the opening angle α not greater than 20° and, particularly, the maximum luminescence intensity is obtained nearly at α=16.2°.

Figure 9:
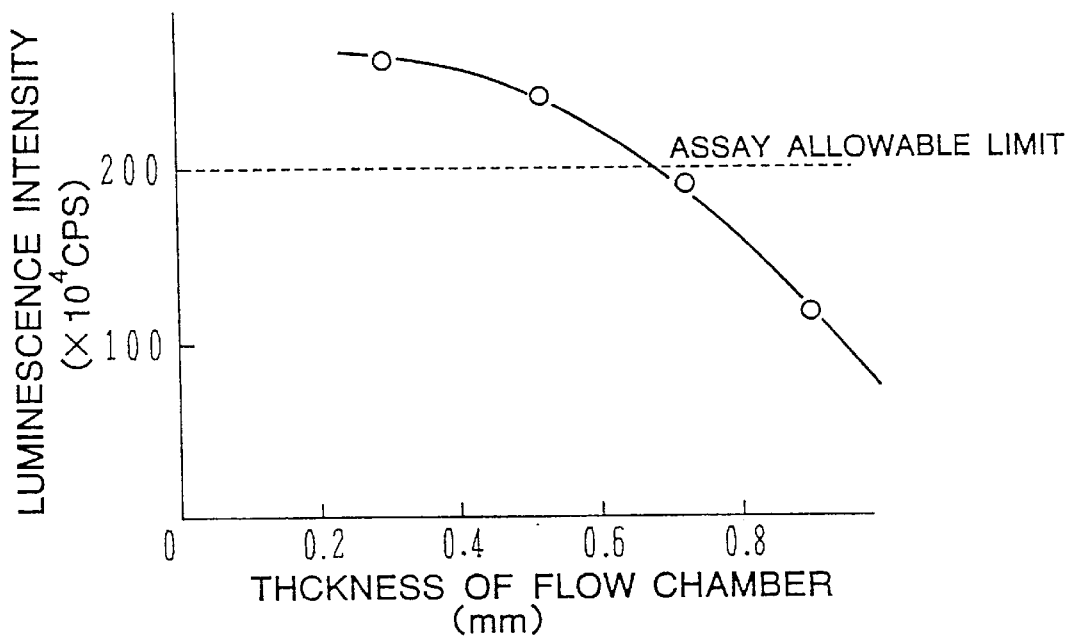
FIG. 9 is a graph of experimental results showing the relationship between the thickness (depth) of the flow chamber and the luminescence intensity.

FIG. 9 shows results of an experiment carried out on the relationship between the thickness t of the flow chamber 17 and the luminescence intensity. The results were obtained by measuring the luminescence intensity while changing the thickness t on condition of the TSH concentration=1×10$^0$ μIU/ml, α=10°, $W_2/W_1$=5, and v=60 mm/s. As will be seen from FIG. 9, the luminescence intensity substantially over 200×10$^4$ cps as an assay allowable limit can be obtained with the thickness t of the flow chamber 17 in the range of 0.3 to 0.7 mm and, particularly, the maximum luminescence intensity is obtained nearly at t=0.5.

Figure 10:
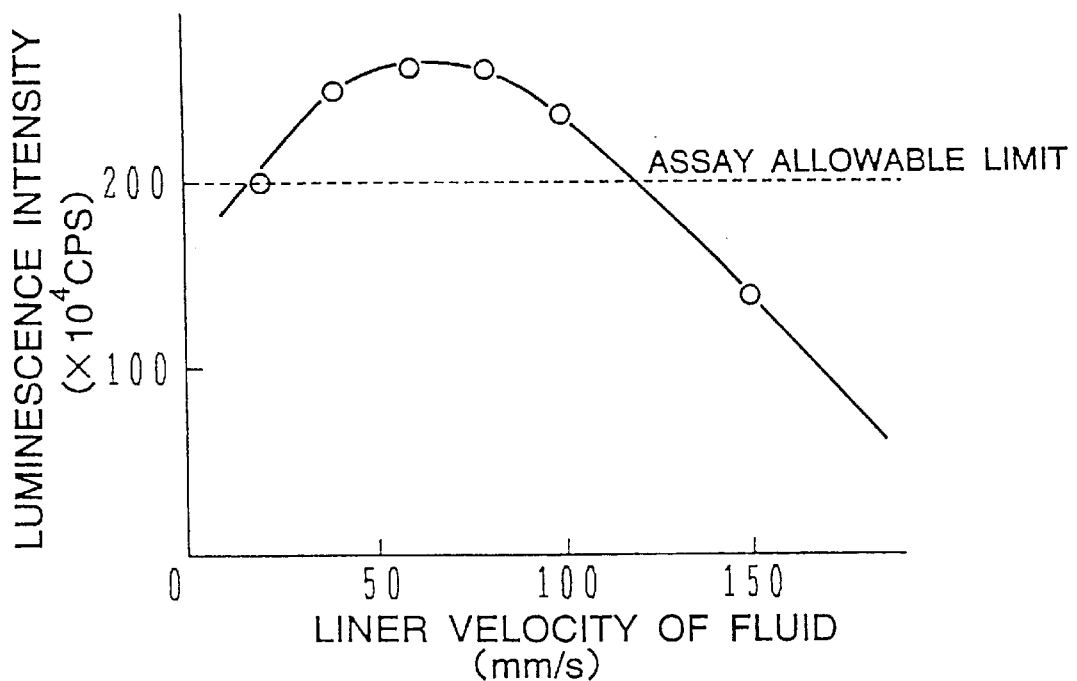
FIG. 10 is a graph of experimental results showing the relationship between the linear velocity at which a reaction mixture flows through the flow chamber and the luminescence intensity.

FIG. 10 shows results of an experiment carried out on the relationship between the linear velocity v of the suspension and the luminescence intensity. The results were obtained by measuring the luminescence intensity while changing the linear velocity v of the suspension on condition of the TSH concentration=1×10$^0$ μIU/ml, α=10°, $W_2/W_1$=5, and t=0.5 mm. As will be seen from FIG. 10, the luminescence intensity substantially over 200×10$^4$ cps as an assay allowable limit can be obtained with the linear velocity v of the suspension introduced to the flow chamber 17 in the range of 10 to 100 mm/s and, particularly, the maximum luminescence intensity is obtained nearly at v=50 mm/s.

Figure 11:
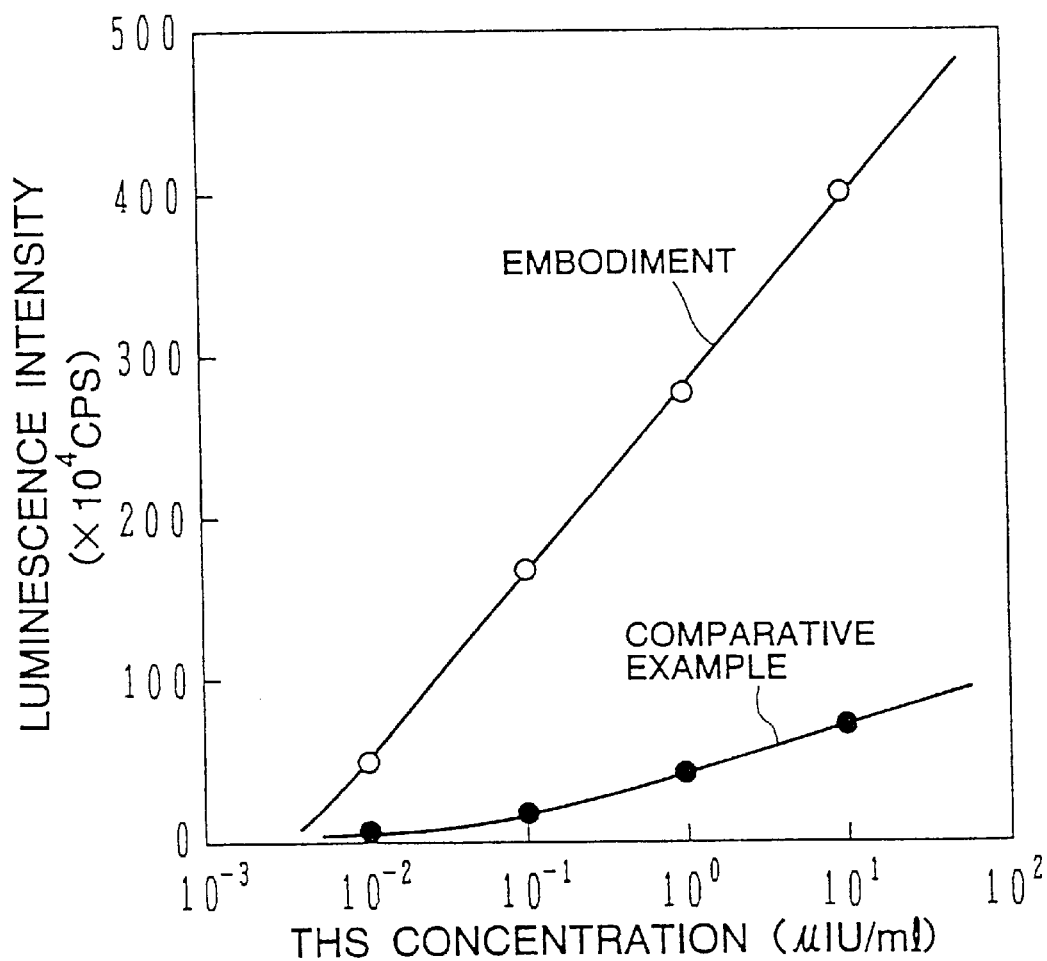
FIG. 11 is a graph showing the relationship between the TSH concentration and the luminescence intensity.
Figure 12:
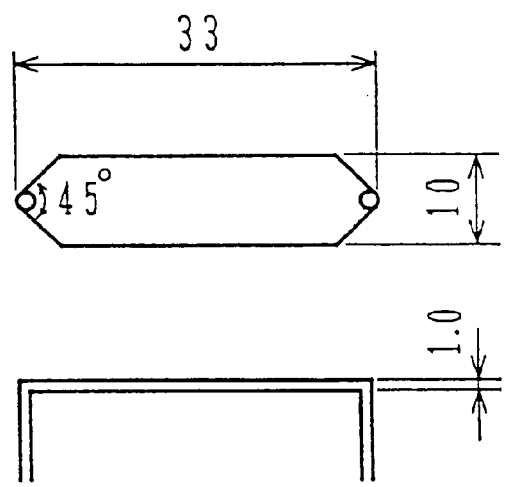
FIG. 12 is a view showing the shape of a flow chamber used in a comparative example.

FIG. 11 shows the relationship of the luminescence intensity with respect to the TSH concentration, which was obtained by the measurement using the above-described steps and the measuring cell 6 of the illustrated embodiment. As a comparative example, FIG. 11 also shows results of the measurement obtained by using a measuring cell in the form of a flow chamber as shown in FIG. 12. The flow chamber of FIG. 12 is formed to have the opening angle α=45°, $W_2/W_1$=10, the linear velocity v of the suspension=60 mm/s, and t=1.0 mm. Also, the comparative flow chamber is shaped to be not spindle-like, but to have a linear central portion. As will be seen from FIG. 12, the above embodiment can provide the calibration curve having a steeper gradient than that resulted from the comparative example, and hence can achieve higher measuring accuracy (sensitivity).

What is claimed is:

1. An immunoassay analyzer comprising:
    a flow through cell having a chamber, the chamber having a plurality of chamber surfaces, the chamber surfaces forming a chamber width of about 2 to about 20 times greater than a chamber depth, an inlet, a maximum width portion positioned between the outlet and the inlet, and a minimum width portion positioned at the inlet, the inlet having an inner diameter equal to the minimum width portion, and the chamber depth being lesser than the inner diameter of the inlet;
    a means for applying a magnetic field to the flow through cell, the means being positioned along one of the chamber surfaces parallel to a horizontal plane in which the chamber width lies;
    a photodetector positioned along one of the chamber surfaces opposite the means for applying a magnetic field and parallel to the horizontal plane in which the chamber width lies, the photodetector for detecting luminescence emitted from fluid flowing through or contained in the chamber; and
    a working electrode and a counter electrode positioned along one of the chamber surfaces, wherein the working electrode has a surface area exposed to the chamber and the means for applying a magnetic field is a magnet having a surface area of about 0.5 to about 3 times the surface area of the working electrode.

2. An immunoassay analyzer according to claim 1, wherein the maximum width portion of the chamber is less than or equal to seven times the minimum width portion of the chamber.

3. An immunoassay analyzer according to claim 1, further comprising a means for controlling the linear velocity of fluid flowing through the chamber and for allowing fluid components to be selectively retained or eliminated from the chamber, the means for controlling the linear velocity of the fluid being connected to the inlet or outlet of the chamber.

4. An immunoassay analyzer according to claim 1, wherein the working electrode is positioned between the magnetic field applying means and the photodetector and is disposed closer to the magnetic field applying means than to the photodetector.

5. An immunoassay analyzer according to claim 4, wherein the magnetic field applying means produces a magnetic pole surface and the shortest distance between the resulting magnetic pole surface and the working electrode is in the range of about 0.5 to about 3.0 mm.

6. An immunoassay analyzer according to claim 1, wherein the magnetic field applying means further comprises a permanent magnet and a means for moving the permanent magnet away from the working electrode prior to applying a voltage between the working electrode and the counter electrode.

* * * * *